(12) United States Patent
Molenda et al.

(10) Patent No.: US 7,988,955 B2
(45) Date of Patent: Aug. 2, 2011

(54) CONDITIONING COMPOSITION

(75) Inventors: Michael Molenda, Frankfurt (DE); Magali Lateulere, Darmstadt (DE)

(73) Assignee: KPSS-KAO Professional Salon Services GmbH, Darmstadt (DE)

( * ) Notice: Subject to any disclaimer, the term of this patent is extended or adjusted under 35 U.S.C. 154(b) by 434 days.

(21) Appl. No.: 11/301,875

(22) Filed: Dec. 13, 2005

(65) Prior Publication Data
US 2006/0130247 A1 Jun. 22, 2006

(30) Foreign Application Priority Data

Dec. 16, 2004 (EP) ..................................... 04029774

(51) Int. Cl.
*A61K 8/49* (2006.01)
*A61Q 5/00* (2006.01)
(52) U.S. Cl. ....................... 424/70.9; 424/70.1; 424/401
(58) Field of Classification Search ................. 424/70.1, 424/401, 70.9
See application file for complete search history.

(56) References Cited

U.S. PATENT DOCUMENTS

| 5,474,762 | A | * | 12/1995 | Carr et al. | ........................ 424/59 |
| 5,656,280 | A | * | 8/1997 | Herb et al. | ..................... 424/401 |
| 5,843,193 | A | | 12/1998 | Hawkins et al. | .................. 8/408 |
| 6,620,410 | B1 | * | 9/2003 | Cho et al. | ..................... 424/70.9 |
| 7,268,105 | B2 | * | 9/2007 | Molenda | ........................ 510/128 |
| 2006/0096041 | A1 | * | 5/2006 | Molenda et al. | .................. 8/405 |
| 2006/0100114 | A1 | * | 5/2006 | Molenda et al. | ............. 510/119 |
| 2006/0130246 | A1 | * | 6/2006 | Molenda et al. | .................. 8/405 |
| 2006/0135393 | A1 | * | 6/2006 | Molenda | ........................ 510/421 |
| 2006/0272105 | A1 | * | 12/2006 | Molenda et al. | .................. 8/405 |

FOREIGN PATENT DOCUMENTS

| DE | 29903100 U1 * | 11/2000 |
| EP | 0 437 006 A1 | 7/1991 |
| WO | WO 03/053386 A1 | 7/2003 |

OTHER PUBLICATIONS

Derwent Acc. No. 2000-657513, Sep. 28, 2000, Abstract. of DE 29903100 U1.*
Goldwell GmbH, "Hair Treatment Composition", Nov. 2, 2000, DE 29903100 U1, English translation (PTO 2009-4079).*

* cited by examiner

*Primary Examiner* — Gina C Yu
(74) *Attorney, Agent, or Firm* — Norris McLaughlin & Marcus, P.A.

(57) ABSTRACT

The present invention is related to stabilization of color of conditioning compositions for hair on aqueous basis, suitable for use after using cleansing compositions by using at least one chelating agent and at least one UV absorbing substance.

9 Claims, No Drawings

CONDITIONING COMPOSITION

The present invention is related to stabilization of color of conditioning compositions for hair on aqueous basis, suitable for use after using cleansing compositions Colorful conditioning compositions have become more and more favorable in the cosmetic market. The colors serve for attractive appearance especially for transparent compositions in a transparent packaging material, as well as, from consumer point of view, helps to identify product and may as well communicate to the consumer product benefit.

For coloring the conditioning compositions, anionic, neutral, cationic and natural dyes or their mixtures are used. Especially preferred ones are the anionic ones.

Stability of color of conditioning composition is an important issue as most of the dyes are decomposing by environmental effects and especially by irradiation to sun and UV rays. In practice, color stabilization is a major subject matter for the formulators of such composition. It has been observed throughout the years that special difficulties exist especially with blue and red dyes.

It has also been observed that color stability problem is aggravated especially when pH of the composition becomes more and more acidic and especially below 4.5.

The present invention starts from such problems mentioned above. Accordingly the object of the present invention is to prevent or at least to diminish color fading without visible colour change or disappearing of the liquid conditioning compositions.

It has surprisingly been found out that a color of the conditioning composition comprising at least one dyestuff selected from anionic, cationic, neutral dyes is stabilized when the composition comprises at least one chelating agent and at least one UV absorber.

Further object of the invention is the use of combination of at least one chelating agent and at least one UV absorbing agent for stabilization of color of conditioning compositions at least one dyestuff selected from anionic, cationic, neutral dyes for hair.

Still further object of the invention is stabilization of color of conditioning compositions for hair comprising at least one dyestuff selected from anionic, cationic, neutral dyes, at least one conditioning agent and at least one dicarboxylic and/or hydroxycarboxylic acid and having a pH value below 4.5, preferably 2 to 4.0 and more preferably 2.8 to 3.8.

In practice the combination of the compounds, at least one chelating agent and at least one UV absorbing compound, stabilizes the color of liquid cleansing compositions at a wider pH range from 2 to 7.

During the experimental studies, it has been found out that when UV absorbing agent and chelating agent are used individually, mostly color stabilization is not observed or the effect is at very low level, if present. Once again the problem is aggravated when the pH of the conditioning composition is acidic and especially below 4.5. When both compounds are contained in the same composition, color of the compositions is stabilized. This shows synergistic effects of the both components.

DE 195 15 698 deals with the stabilization of the color of liquid cleansing compositions and provides as a solution the use of a known antimicrobial agent pyrithion or its salts at a lower concentration range. The document is silent on use of any combination as provided with the present invention and especially for any hair conditioning composition designed for using after use of cleansing preparations.

The chelating agents useful within the frame of the present invention are beta-alanine diacetic acid, aminotrimethylene phosphoric acid, citric acid, ethylendiamine tetra acetic acid, cyclohexanediamine tetraacetic acid, etidronic acid, galactaric acid, galacturonic acid, gluconic acid, glucuronic acid, pentetic acid, phytic acid and any of their sodium potassium salts. Among those etidronic acid and ethylenediamine tetraacetic acid and their potassium and sodium salts or their mixtures are the preferred ones. Most preferred is the EDTA and its mono, di, tri or tetra sodium or potassium salts or their mixtures.

The concentration of chelating agent is in the range of 0.01 to 5%, preferably 0.05 to 4% and more preferably 0.05 to 3% and most preferably 0.05 to 2.5% by weight calculated to the total compositions.

The UV filters are those oil and water soluble ones for the purpose of the present invention. In other words, anionic and nonionic, oily or oil soluble, UV filters are suitably used in the compositions of the present invention. Suitable UV-absorbing substances are: 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2.4-dihydroxybenzophenone, 2.2'.4.4'-tetrahydroxy-benzophenone, 2-hydroxy-4-methoxybenzophenone and its 5-sulfonic acid or the sodium salt thereof, 2.2'-dihydroxy-4.4'-dimethoxybenzophenone, 2-hydroxy-5-chlorobenzophenone, 2.2'-dihydroxy-4-methoxybenzophenone, 2.2'-dihydroxy-4.4'-dimethoxy-5.5'-disulfobenzophenone or the sodium salt thereof, 2-hydroxy-4-octyloxybenzophenone, 2-hydroxy-4-methoxy-4'-methylbenzophenone, 3-benzylidenecampher, 3-(4'-sulfo)-benzyl-idenebornane-2-one and the salts thereof, 3-(4'-methyl benzylidene)-DL-campher and/or benzotriazolyl dodecyl p-cresol. Compositions of the present invention comprise at least one UV absorbing substance and may comprise more than one when needed. The most preferred UV absorbers are benzotriazolyl dodecyl p-cresol (known with the trade name Tinogard TL), Benzophenone-3 and Benzophenone-4. The amount of the UV-absorber ranges typically from about 0.01% to 2.5%, preferably from 0.05% to 2, more preferably 0.05 to 1.5 and most preferably 0.05 to 1% % by weight, calculated to the total composition.

According to the invention, the conditioning compositions are colored with anionic, neutral, cationic or natural dyestuffs or their combinations. The suitable anionic dyestuffs are any usable for cosmetic purposes and especially those available for product colouring purposes. Without limiting possibility of using other not listed ones, examples of the suitable anionic dyes are: Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

As the dyes used for colouring the composition and not having any dyeing effect on the surface of the object treated with it, their concentration is usually quite low and in any case lower than 0.25%, preferably lower than 0.2% and more preferably lower than 0.15% and most preferably lower than 0.1% by weight calculated to the total composition. It should be noted that in the case of dark dyestuffs such as blue, red or any other darker direction the concentration may also be in the ppm range. The concentrations mentioned here are total dyestuff concentration and not refer to the individual dyes.

Although not the first choice for the purpose of product colouring, conditioning compositions may also be coloured with cationic dyes. Their substantivity to the negatively charged surfaces because of their cationic nature should be kept in mind when using the dyes. Those dyes are especially used as direct dyes in conditioning and colouring compositions for hair. Some examples again without limiting the selection are: Basic Blue 6, Basic Blue 7, Basic Blue 9, Basic Blue 26, Basic Blue 41, Basic Blue 99, Basic Brown 4, Basic Brown 16, Basic Brown 17, Basic Orange 31, Natural Brown 7, Basic Green 1, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87. The concentration of the cationic dyes should be kept very low.

Additionally, the conditioning compositions may also be colored with neutral dyes (HC dyes), so called nitro dyes. Here again their substantivity to the surfaces should be taken into consideration when using the dyestuffs. Hair conditioning compositions are particularly mentioned in this concern. The concentration the neutral dyes should preferably be very low. Some of the neutral dyes to mention, without limiting the selection or the use of the not mentioned ones are: HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Plant dyestuffs may also be used for coloring liquid cleansing compositions for example henna (red or black), alkanna root, laccaic acid, indigo, logwood powder, madder root and rhubarb powder, etc.

It should be noted that anionic, cationic, neutral and plant (natural) dyes are as well used in combination with each other.

The concentration of total dyestuffs, one or more and in mixture with any other either anionic, or cationic, or neutral or natural, is lower than 0.25%, preferably lower than 0.2% and more preferably lower than 0.15% and most preferably lower than 0.1% by weight calculated to the total composition. As the subject matter of the present invention is colour stabilization, the composition in any case comprise one or more dyestuffs and the concentration can be as low as 0.00001% by weight calculated to total composition.

Among all the dyestuffs disclosed above, anionic dyes are found to be the most suitable and preferred ones.

Conditioning compositions of the present invention comprise at least one hair-conditioning compound. Suitable ones are those of cationic compounds, especially cationic polymers and cationic surfactants. Oily substances and non-ionic substances can as well be suitably used as conditioners in the compositions of the present invention.

Suitable cationic polymers are those of best known with their CTFA category name Polyquaternium. Typical examples of those Polyquaternium 6, Polyquaternium 7, Polyquaternium 10, Polyquaternium 11, Polyquaternium 16, Polyquaternium 22 and Polyquaternium 28.

As well those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-81, Quaternium-82, Quaternium-83 and Quaternium-84.

It has further been found out that especially those of cationic cellulose type polymers known as Polymer JR type from Amerchol such as Polyquaternium 10 or cationic guar gum known with trade name Jaguar from Rhône-Poulenc and chemically for example Guar hydroxypropyl trimonium chloride, are preferred ones. Furthermore, chitosan and chitin can also be included in the compositions as cationic natural polymers. In this context reference is also made to the cationic polymers disclosed in DE 25 21 960, 28 11 010, 30 44 738 and 32 17 059, as well as to the products described in EP-A 337 354 on pages 3 to 7. It is also possible to use mixtures of various cationic polymers.

The most preferred cationic polymers are those of cationic cellulose derivatives, cationic guar gum derivatives, polyquaternium 6 and polyquaternium 7.

The cationic polymers also include the quaternized products of graft polymers from organopolysiloxanes and polyethyl oxazolines described in EP-A 524 612 and EP-A 640 643.

Typical concentration range for cationic polymers is 0.01-5% by weight, preferably 0.01-3.5% by weight, more preferably 0.05-2.5% and most preferably 0.05-1.5% by weight calculated to the total composition.

In one of the preferred from of the present invention, conditioning compositions comprise at least one cationic surfactant as conditioning agent and as well as emulsifier. Suitable cationic surfactants are presented with the general formula

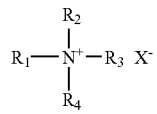

where $R_1$ is a saturated or unsaturated, branched or non-branched alkyl chain with 8-22 C atoms or

where $R_5$ is saturated or unsaturated, branched or non-branched alkyl chain with 7-21 C atoms and n has value of 1-4, or

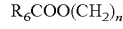

where $R_6$ is saturated or unsaturated, branched or non-branched alkyl chain with 7-21 C atoms and n has value of 1-4, and $R_2$ is H or unsaturated or saturated, branched or non-branched alkyl chain with 1-4 C atoms or

or

where $R_5$, $R_6$ and n are same as above.

$R_3$ and $R_{14}$ are H or lower alkyl chain with 1 to 4 carbon atoms, and X is anion such as chloride, bromide, methosulfate.

Typical examples of those ingredients are cetyltrimethyl ammonium chloride, steartrimonium chloride, behentrimoinium chloride, stearamidopropyl trimonuim chloride, dioleoylethyl dimethyl ammonium methosulfate, dioleoylethyl hydroxyethylmonium methosulfate.

From the above quaternary ammonium compounds disclosed with the general formula, especially to mention are those compounds known per se and are on the market, for example, under the trade names "Schercoquat®", "Dehyquart® F30" and "Tetranyl®". Use of these compounds, the so-called "esterquats", in hair care compositions is described, for example, in WO-A 93/107 48, WO-A 92/068 99 and WO-A 94/166 77, wherein, however, there is no reference made to the combinations according to the present invention and the advantageous properties thereof.

Again from the above quaternary ammonium compounds disclosed with the general formula, especially to metion are these compounds are known per se and on the market, for example, under the trade name "INCROQUAT® HO" or "OCS". Those compounds are known with a general ingredient category under "amidoquat" in the cosmetic industry.

Amido amines may as well be used as a conditioning cationic surfactant in the compositions of the present invention. Typical non-limiting example is stearamidopropylamine known with a trade name Tego Amid S18 from Goldschmidt.

Typical concentration range for cationic surfactants is 0.01-5% by weight, preferably 0.01-3.5% by weight, more preferably 0.05-2.5% and most preferably 0.05-1.5% by weight calculated to the total composition. Accordingly, the total cationic conditioning compound concentration in the compositions of the present invention varies from 0.01 to 5% by weight, preferably 0.01 to 3.5% by weight, more preferably 0.05 to 2.5% and most preferably 0.05 to 1.5% by weight calculated to the total composition It is as well the preferred embodiment of the invention that the cationic surfactants and cationic polymers used in combination at any ratio.

Oily substances are selected from such as silicone oils, either volatile or non-volatile, natural and synthetic oils. Among silicone oils those can be added to the compositions include dimethicone, amodimethicone (a cationic silicone), dimethiconol, polydimethylsiloxane, DC fluid ranges from Dow Corning, natural oils such as olive oil, almond oil, avocado oil, weizenkeim oil, ricinus oil and the synthetic oils, such as mineral oil, isopropyl myristate, palmitate, stearate and isostearate, oleyl oleate, isocetyl stearate, hexyl laurate, dibutyl adipate, dioctyl adipate, myristyl myristate and oleyl erucate.

Non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula

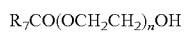

where $R_7$ and $R_8$ are independent from each other saturated, unsaturated or branched or non-branched alkyl chain with 7 to 21 C atoms and n is typically 2-100.

The compositions according to the invention may also comprise further conditioning substances such as protein hydrolyzates and polypeptides, e.g., keratin hydrolyzates, collagen hydrolyzates of the type "Nutrilan®" or elastin hydrolyzates, as well as also in particular plant protein hydrolyzates, optionally, cationized protein hydrolyzates, e.g., "Gluadin®".

Further conditioning additives are hair conditioning and/or styling polymers. These may be nonionic polymers, preferably alcohol- and/or water-soluble vinyl pyrrolidone polymers, such as a vinyl pyrrolidone homopolymers or copolymers, in particular with vinyl acetate. Useful vinyl pyrrolidone polymers are, e.g., those known by the trade name "Luviskol®", for example, the homopolymers "Luviskol® K 30, K 60 and K 90", as well as the water- or alcohol-soluble copolymers from vinyl pyrrolidone and vinyl acetate, distributed by BASF AG under the trade name "Luviskol® VA 55 respectively VA 64". Further possible nonionic polymers are vinyl pyrrolidone/vinyl acetate/vinyl propionate copolymers such as "Luviskol® VAP 343", vinyl pyrrolidone/(meth)acrylic acid ester copolymers, as well as chitosan derivatives.

Amphoteric polymers are found to be useful in conditioning composition of the present invention. They are incorporated alone or in admixture with at least one additional cationic, nonionic or anionic polymer, particularly copolymers of N-octyl acrylamide, (meth)acrylic acid and tert.-butyl aminoethyl methacrylate of the type "Amphomer®"; copolymers from methacryl oylethyl betaine and alkyl methacrylates of the type "Yukaformer®", e.g., the butyl methacrylate copolymer "Yukaformer® Am75"; copolymers from monomers containing carboxyl groups and sulfonic groups, e.g., (meth) acrylic acid and itaconic acid, with monomers such as mono- or dialkyl amino alkyl(meth)acrylates or mono- or dialkylaminoalkyl (meth)acrylamides containing basic groups, in particular amino groups; copolymers from N-octyl acrylamide, methyl methacrylate, hydroxypropyl methacrylate, N-tert.-butyl aminoethyl methacrylate and acrylic acid, as well as the copolymers known from U.S. Pat. No. 3,927,199, are applicable.

Conditioning compositions of the present invention can be in the form of emulsions, solutions, gels and dispersions. In the case that solutions and/or gels forms are prefered the appearance can be either with a transparent or opaque. Transparency of the composition is judged by naked eye in a transparent bottle with a thickness not more than 5 cm. As a product form, foam is as well suited when packed into a pressurized can or delivered through a pump-foamer (non-aerosol). In the case that an aerosol foam preparation is preferred, propellant gas must be added to the formulation. The suitable propellant gasses are carbondioxide, dimethylether and alkanes such as butane, propane, isobutane or their mixtures.

The emulsion type of conditioners comprise additionally at least one fatty alcohol of the following formula

where $R_9$ is a saturated or unsaturated, branched or non-branched fatty acyl chain with 8-24 C atoms. Concentration of fatty alcohol is usually less than 20%, preferably less than 15% by weight calculated to total composition. Typical examples to the most useful fatty alcohols are myristyl alcohol, palmityl alcohol, cetyl alcohol, stearyl alcohol, behenyl alcohol and their mixtures. As a mixed fatty alcohol the mostly used one is the cetearyl alcohol as well preferred in the compositions of the present invention.

The composition of the present invention can comprise surface-active substances as emulsifiers other than cationic surfactants disclosed above especially when an emulsion is preferred. These can be anionic and/or nonionic and/or amphoteric or zwitterionic and/or their mixtures incorporated at a concentration ranging between 0.1-10%, preferably 0.1-7.5% and more preferably 0.1-5% by weight calculated to the total composition. Preferred emulsifiers are of non-ionic surfactants in addition to the cationic ones. The anionic ones are as a rule not preferred and if their presence is desirable because of any reason, those should form the very minor part, as electrostatic interactions with the cationic material especially cationic conditioners either surfactants or polymers can disturb the stability of those conditioners. Zwitterionic ones are also the ones preferred to lesser extent.

Suitable preferred nonionic surfactants useful in the compositions according to invention are $C_{10}$-$C_{22}$-fatty alcohol ethoxylates. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16":

The average degree of ethoxylation thereby ranges between about 2.5 and about 25, preferably about 10 and about 20.

Further suitable nonionic surfactants according to the invention are alkyl polyglucosides of the general formula

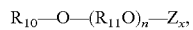

wherein $R_{10}$ is an alkyl group with 8 to 18 carbon atoms, $R_{11}$ is an ethylene or propylene group, Z is a saccharide group with 5 to 6 carbon atoms, n is a number from 0 to 10 and x is a number between 1 and 5.

Further nonionic surfactants are, for example, long-chain fatty acid mono- and dialkanolamides, such as coco fatty acid monoethanolamide and myristic fatty acid monoethanolamide.

Further useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates.

Further suitable nonionic surfactants are amineoxides. Such amineoxides are state of the art, for example $C_{12}$-$C_{18}$-alkyl dimethyl amineoxides such as lauryl dimethyl amineoxide, $C_{12}$-$C_{18}$-alkyl amidopropyl or -ethyl amineoxides, $C_{12}$-$C_{18}$-alkyl di(hydroxyethyl) or (hydroxypropyl) amineoxides, or also amineoxides with ethyleneoxide and/or propyleneoxide groups in the alkyl chain. Such amineoxides are on the market, for example, under the trade names "Ammonyx®", "Aromox®" or "Genaminox®".

As further surfactant component, the compositions according to the invention can also contain amphoteric or zwitterionic surfactants. Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

Anionic surfactants are as a rule preferred to a lesser extend. Some of them are to mention those of sulfate, sulfonate, carboxylate and alkyl phosphate types. Examples are the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates.

Additional anionic surfactants are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Further anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

The pH of the compositions according to the present invention is below 4.5 and preferably in the range of 2.0 to 4.0, more preferably 2.5 to 4.0, most preferably 2.5 to 3.80.

In principal pH of the compositions can be adjusted with any organic and/or inorganic acids or their mixture. Some of them to mention are phosphoric acid, hydrochloric acid as the inorganic ones and to the organic acids the well known citric acid. However the best hair conditioning effects are observed when the carboxylic acids and especially those of with hydroxycarboxylic acids and/or dicarboxylic acids are included into the composition for adjusting pH. Accordingly the pH of the compositions is adjusted with hydroxycarboxylic acids and/or dicarboxylic acids. In those cases where selected hydroxycarboxylic acid and/or dicarboxylic acid concentration is not enough to reach the selected pH, other organic and inorganic acids may as well be used to adjust pH to the required value. The hydroxycarboxylic acids useful in the compositions of the present invention are lactic acid, glycolic acid, hydroxyacrylic acid, glyceric acid, malic acid and tartaric acid and of the dicarboxylic acids are malonic acid, succinic acid, glutaric acid, adipic acid, maleic acid, fumaric acid and phtalic acid.

Compositions according to present invention comprise preferably at least one hydroxycarboxylic acid and/or dicarboxylic acid. Combinations of two or more hydroxycarboxylic acids and/or dicarboxylic acids are also within the scope of the invention. It should be noted that mixture of two or more hydroxycarboxylic acid and dicarboxylic acid comprising compositions are also within the scope of the present invention. Especially preferred hydroxycarboxylic acids are the lactic and malic acids. Malic acid is also a dicarboxylic acid. The most preferred hydroxycarboxylic acid and/or dicarboxylic acid is the malic acid.

Total hydroxycarboxylic acid and/or dicarboxylic acid concentration in the composition of the present invention varies in the range form 0.1 to 5% by weight, preferably 0.25 to 3% by weight, more preferably 0.5 to 3% by weight and most preferably 0.75 to 3% by weight. In a preferred embodiment of the invention, the compositions of the present invention comprise at least 0.5% malic acid.

In another preferred form of the invention, it has been found out that in the presence of organic solvents, the effects especially the shine enhancing effect of the compositions is very much enhanced. Without being bound by any theory, it is thought that the accelerated/more pronounced effect is observed due to penetration enhancing effect of the organic solvents. Accordingly, compositions can comprise organic solvents such as ethanol, propanol, isopropanol, benzyl alcohol, benzyloxyethanol, ethoxydiglycol, alkylene carbonates such as ethylene carbonate and propylene carbonate, phenoxyethanol, butanol, isobutanol, cyclohexane, cyclohexanol, hexyleneglycol, ethylenecarbonate, propyleneglycol, poypropyleneglycols, ethyleneglycol monoethylether, ethylene glycol monobutyl ether, ethylene glycol monophenyl ether, 1-phenylethylalcohol, 2-phenylethylalcohol, o-methoxyphenol. The most preferred ones are benzylalcohol, benzyloxyethanol, ethanol and polypropylene glycols. Concentration of organic solvents in the compositions should not exceed 10% by weight, preferably in the range of 0.1 to 7.5%, more preferably 0.2 to 5% by weight calculated to total composition.

The viscosity of the compositions depends on the type of application according to the invention. Emulsion type of compositions have the viscosity in the range of between about 1000 and about 50,000 mPa·s at 20° C., measured according to Brookfield Rheometer at a shear rate of 10 sec$^{-1}$. Whereas compositions dispensed form an aerosol and/or pump foamer should preferably be very liquid, i.e. viscosity values not more than approximately 500 mPa·s measured as given above are not appropriate.

Compositions of the present invention are used especially after shampooing and can be applied to hair either as a leave-in or as a rinse off compositions.

Furthermore, compositions of the present invention can comprise all substances customarily found in hair conditioning preparations.

Examples of such substances are natural plant extracts, preservatives, fragrances, moisturizers, etc.

Natural plant extracts are incorporated usually in an amount of about 0.01% to about 10%, preferably 0.05% to 7.5%, in particular 0.1% to 5% by weight, calculated as dry residue thereof to the total composition. Suitable aqueous (e.g. steam-distilled) alcoholic or hydro-alcoholic plant extracts known per se are in particular extracts from leaves, fruits, blossoms, roots, rinds or stems of aloe, pineapple, artichoke, arnica, avocado, valerian, bamboo, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, cocoanut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc.

Suitable trade products are, for example, the various "Extrapon®" products, "Herbasol®" "Sedaplant®" and "Hexaplant®". Extracts and the preparation thereof are also described in "Hagers Handbuch der pharmazeutischen Praxis", 4$^{th}$ Ed.

The moisturizing agents are selected from panthenol, polyols, such as glycerol, polyethylene glycols with molecular weight 200 to 20,000. The moisturizing ingredients can be included in the conditioner compositions at a concentration range of 0.01-2.5% by weight calculated to the total composition.

Measurement of Color Stability

UV light and sun light stability was determined in a polyethylene terphtalate (PET-P) bottle with a weight of 24.5±0.5 g per 200 ml filling volume by using a UV light irradiation equipment named Sunset Machine model Sunset CPS supplied by Atlas Material Testing Solution. Light emission energy of the equipment is 765 W/m$^2$±10%. The bottles used do not contain any UV absorbing substance. Temperature during the measurement was around 46° C.±2° C. Bottle used had a volume of around 200 ml and a surface area of 0.0108 m$^2$ is usually exposed to UV light for 30 h which corresponds to 892 kJ.

In addition to this, the bottles were exposed to direct sunlight on the roof of a building and using a 1 cm$^2$ photocell the produced electro energy is measured in Watt. A computing device (counter)—purchased from Kipp & Zonen—Radiation indicator CC20—reported on the display the energy exposure of the bottled compositions in Wh/m2. The length of the exposure was set at the value 30.000 Wh/m$^2$ which is approximately equal to the 892 kJ as in the case of UV light stability measurement. During the tests the same bottles were used as mention in the UV test part.

Finally the color measurements were carried out before and after exposure to UV light or sun light using a Minolta laboratory color measuring device directly in the PET-P bottle and color differences were obtained.

The following hair conditioning composition was used throughout the experimental work for determination of color stability.

| Hair conditioning composition | |
| --- | --- |
| Cetylstearylalcohol | 5.0 (% by weight) |
| Stearyltrimethylammoniumchlorid | 0.7 |
| Dioleoylethyl dimethyl ammonium methosulfate | 0.5 |
| Silicone oil (Dimethicone) | 0.6 |
| Isopropylmyristate | 0.4 |
| Panthenol | 0.2 |
| Benzylalcololol | 1.0 |
| Propyleneglycol | 0.8 |
| Lactic acid | 0.2 |
| Fragrance, preservative | q.s. |
| Malic acid | 1.0 |
| Sodium hydroxide | q.s pH 3.3 |
| Wasser | ad 100.0 |

EXAMPLE 1

Acid violet 43 was used at a concentration of 0.0028% by weight which was introduced into the composition from a stock solution in water containing 0.1% acid red 52.

4 composition were examined for their color stability as follows:

Composition A not comprising any chelating and UV absorbing agent

Composition B comprising only chelating agent EDTA at a concentration of 0.1% by weight Composition C comprising only UV absorbing agent benzotriazolyl dodecyl p-cresol (Tinogard TL) at a concentration of 0.1% by weight Composition D comprising both chelating agent EDTA and UV absorbing agent benzotriazolyl dodecyl p-cresol (Tinogard TL) both at a concentration of 0.1% by weight.

The conditioning composition obtained were exposed to UV light as described above in a 200 ml PET-P bottle. Before and after 30 hrs of exposure, the color measurements, L, a and b values, were carried out with the color measuring device mentioned above. From the L, a and b data ΔE values are calculated using the known formula.

The following results were obtained

| Composition | ΔE |
|---|---|
| 1-A | 17.6 |
| 1-B | 9.2 |
| 1-C | 10.2 |
| 1-D | 4.2 |

EXAMPLE 2

The same as described under Example 1 was carried out using Basic red 51 a cationic dyestuff at a concentration of 0.0012% by weight. Same as in the Example 1 the conditioning compositions were exposed to UV light as described above in a 200 ml PET-P bottle. The compositions tested were:

Composition A not comprising any chelating and UV absorbing agent

Composition B comprising only chelating agent EDTA at a concentration of 0.1% by weight Composition C comprising only UV absorbing agent benzotriazolyl dodecyl p-cresol (Tinogard TL) at a concentration of 0.1% by weight Composition D comprising both chelating agent EDTA and UV absorbing agent benzotriazolyl dodecyl p-cresol (Tinogard TL) both at a concentration of 0.1% by weight.

The following results were obtained

| Composition | ΔE |
|---|---|
| 3-A | 21.3 |
| 3-B | 18.8 |
| 3-C | 19.4 |
| 3-D | 2.5 |

Similar results were obtained with the other dyestuffs mentioned in the description.

The invention claimed is:

1. Conditioning composition comprising at least one hair conditioning compound, at least one direct dyestuff selected from cationic, anionic, neutral and natural plant direct dyes, at least one chelating agent selected from the group consisting of ethylenediaminetetraacetic acid, ethylenediaminetetraacetic acid salts and mixtures thereof, and benzotriazolyl dodecyl p-cresol, wherein the composition has a pH between 2 and 4.5 and the composition is an emulsion comprising at least one fatty alcohol and at least one emulsifier.

2. Composition according to claim 1 characterized in that it comprises at least one anionic dye.

3. Composition according to claim 1 characterized in that it comprises as a conditioning compound at least one cationic polymer and/or at least one cationic surfactant.

4. Composition according claim 1 characterized in that it comprises as an emulsifier at least one nonionic surfactant.

5. Composition according to claim 1 characterized in that it is a transparent composition.

6. Composition according to claim 1 characterized in that it comprises additionally at least one hydroxycarboxylic acid and/or dicarboxylic acid.

7. Composition according to claim 6 characterized in that it comprises at least one dicarboxylic acid and/or hydroxycarboxylic acid at a concentration of 0.1 to 5% by weight calculated to total composition.

8. Composition according to claim 7 it comprises hydroxycarboxylic acid at a concentration of 0.5 to 5% by weight with the condition that it comprises malic acid at a concentration of not less than 0.5% by weight calculated to total composition.

9. Composition according to claim 1 characterized in that it comprises organic solvents at a concentration of less than 10% by weight calculated to total concentration.

* * * * *